(12) United States Patent
Utsumi et al.

(10) Patent No.: US 10,216,084 B2
(45) Date of Patent: Feb. 26, 2019

(54) SULFONIC ACID DERIVATIVE, PHOTOACID GENERATOR USING SAME, RESIST COMPOSITION, AND DEVICE MANUFACTURING METHOD

(71) Applicant: TOYO GOSEI CO., LTD., Ichikawa-shi, Chiba (JP)

(72) Inventors: Yoshiyuki Utsumi, Ichikawa (JP); Noriaki Kobayashi, Ichikawa (JP); Takahiro Kamakura, Ichikawa (JP)

(73) Assignee: Toyo Gosei Co., Ltd., Ichikawa-Shi, Chiba (JP)

( * ) Notice: Subject to any disclaimer, the term of this patent is extended or adjusted under 35 U.S.C. 154(b) by 0 days.

(21) Appl. No.: 15/533,340

(22) PCT Filed: Nov. 26, 2015

(86) PCT No.: PCT/JP2015/083264
§ 371 (c)(1),
(2) Date: Jun. 5, 2017

(87) PCT Pub. No.: WO2016/088648
PCT Pub. Date: Jun. 9, 2016

(65) Prior Publication Data
US 2018/0011401 A1 Jan. 11, 2018

(30) Foreign Application Priority Data
Dec. 5, 2014 (JP) .................................. 2014-247414

(51) Int. Cl.
| | | |
|---|---|---|
| *G03F 7/004* | (2006.01) |
| *G03F 7/30* | (2006.01) |
| *G03F 7/40* | (2006.01) |
| *C07C 309/04* | (2006.01) |
| *C07C 309/06* | (2006.01) |
| *C07C 309/08* | (2006.01) |
| *C07C 309/12* | (2006.01) |
| *C07C 309/19* | (2006.01) |
| *C07C 309/24* | (2006.01) |
| *C07C 303/32* | (2006.01) |
| *C07C 381/12* | (2006.01) |
| *C09K 3/00* | (2006.01) |
| *H01L 21/027* | (2006.01) |
| *G03F 7/16* | (2006.01) |
| *G03F 7/20* | (2006.01) |

(52) U.S. Cl.
CPC .......... *G03F 7/0045* (2013.01); *C07C 303/32* (2013.01); *C07C 309/04* (2013.01); *C07C 309/06* (2013.01); *C07C 309/08* (2013.01); *C07C 309/12* (2013.01); *C07C 309/19* (2013.01); *C07C 309/24* (2013.01); *C07C 381/12* (2013.01); *C09K 3/00* (2013.01); *G03F 7/004* (2013.01); *H01L 21/027* (2013.01); *C07C 2603/74* (2017.05); *G03F 7/16* (2013.01); *G03F 7/20* (2013.01); *G03F 7/30* (2013.01)

(58) Field of Classification Search
CPC ... G03F 7/0045; G03F 7/0397; C07C 303/32; C07C 309/04; C07C 309/06; C07C 309/08; C07C 309/19; C07C 309/24
USPC ....... 430/270.1, 326, 921; 562/42, 100, 108, 562/109, 113
See application file for complete search history.

(56) References Cited

U.S. PATENT DOCUMENTS

| | | | |
|---|---|---|---|
| 2008/0254386 A1 | 10/2008 | Nishi et al. | |
| 2010/0323294 A1 | 12/2010 | Li et al. | |
| 2011/0217654 A1* | 9/2011 | Yamato | C07C 271/24 430/270.1 |
| 2012/0141939 A1* | 6/2012 | Thackeray | G03F 7/0045 430/285.1 |
| 2012/0164582 A1* | 6/2012 | Maruyama | C07C 307/06 430/285.1 |
| 2012/0289738 A1* | 11/2012 | Hosoi | C07C 309/12 562/42 |
| 2013/0065186 A1 | 3/2013 | Matsuda et al. | |
| 2015/0093708 A1 | 4/2015 | Labeaume | |

FOREIGN PATENT DOCUMENTS

| | | |
|---|---|---|
| CN | 101930173 A | 12/2010 |
| CN | 102781911 A | 11/2012 |
| CN | 104570602 A | 4/2015 |
| EP | 2267532 A1 | 12/2010 |
| EP | 2539316 A1 | 1/2013 |
| JP | 10007650 A | 1/1998 |
| JP | 2003327572 A | 11/2003 |
| JP | 2008007410 A | 1/2008 |
| JP | 2008170535 A | 7/2008 |
| JP | 2011090284 A | 5/2011 |
| JP | 2013520458 A | 6/2013 |
| JP | 2014222338 A | 11/2014 |
| JP | 2015-007048 A | 1/2015 |
| JP | 2015091935 | 5/2015 |
| JP | 2015-147772 A | 8/2015 |
| KR | 10-2008-0065550 A | 7/2008 |
| KR | 10-2010-0137393 A | 12/2010 |

(Continued)

OTHER PUBLICATIONS

PCT International Search Report dated Feb. 17, 2016, dated Mar. 1, 2016, PCT/JP2015/083264.

(Continued)

*Primary Examiner* — John S Chu
(74) *Attorney, Agent, or Firm* — TraskBritt, P.C.

(57) ABSTRACT

A sulfonic acid derivative, wherein the sulfonic acid derivative is represented by the following general formula (1):

$$R^1COOCH_2CH_2CFHCF_2SO_3^-M^+ \quad (1)$$

where: $R^1$ represents a monovalent organic group having carbon number of 1 to 200, having at least one hydroxyl group and optionally having a substituent other than the hydroxyl group; and $M^+$ represents a counter cation.

10 Claims, No Drawings

(56) References Cited

FOREIGN PATENT DOCUMENTS

| KR | 10-2012-0115523 | A | 10/2012 |
|----|-----------------|---|---------|
| KR | 10-2012-0123716 | A | 11/2012 |
| KR | 10-2012-0128680 | A | 11/2012 |
| KR | 10-2015-0035454 | A | 4/2015 |
| WO | 2011104127 | A1 | 9/2011 |
| WO | 2011115138 | A1 | 9/2011 |
| WO | 2015083264 | A1 | 6/2015 |
| WO | 2016088648 | A1 | 6/2016 |
| WO | 2011093139 | | 1/2017 |

OTHER PUBLICATIONS

PCT International Written Opinion dated Mar. 1, 2016, PCT/JP2015/083264, no english translation.
Korean Office action for copending Korean Application No. 10-2017-7014149 dated Apr. 16, 2018, with English translation version.

* cited by examiner

SULFONIC ACID DERIVATIVE, PHOTOACID GENERATOR USING SAME, RESIST COMPOSITION, AND DEVICE MANUFACTURING METHOD

CROSS-REFERENCE TO RELATED APPLICATIONS

This application is a national phase entry under 35 U.S.C. § 371 of International Patent Application PCT/JP2015/083264, filed Nov. 26, 2015, designating the United States of America and published as International Patent Publication WO 2016/088648 A1 on Jun. 9, 2016, which claims the benefit under Article 8 of the Patent Cooperation Treaty to Japanese Patent Application Serial No. 2014-247414, filed Dec. 5, 2014.

TECHNICAL FIELD

Some aspects of this application relate to a sulfonic acid derivative useful as a photoacid generator for a chemically amplified photoresist composition. In addition, some aspects of this disclosure relate to a photoacid generator that is easily decomposed by active energy ray irradiation, such as with deep UV, KrF excimer laser light, ArF excimer laser light, $F_2$ excimer laser light, electron beams, X-rays, or EUV (extreme UV) and generates an acid.

BACKGROUND

In semiconductor devices represented by, for example, highly integrated circuit elements such as DRAM, there has been a great demand for even higher density, higher integration, and higher speed. Accordingly, in the production fields of various electronic devices, requirements for the establishment of fine processing technology of half-micron order, for example, the development of photolithography technology for fine pattern formation, are becoming more and more severe. In photolithography technology, the formation of a fine pattern requires improved resolution. Here, the resolution (R) of a reduced-projection light exposure device is represented by the Rayleigh's equation $R=k \cdot \lambda / NA$ (where $\lambda$ is the wavelength of the exposure light, NA is the numerical aperture of the lens, and k is a process factor). By shortening the wavelength $\lambda$ of the active energy ray (exposure light) used for the formation of a resist pattern, the resolution can be improved.

As photoresists suitable for short wavelengths, chemically amplified photoresists have been proposed. A chemically amplified photoresist is characterized in that when irradiated with exposure light, a protonic acid is generated from a photoacid generator, which is a component contained in the photoresist, and, as a result of a heating treatment after exposure to light, the protonic acid undergoes an acid-catalyzed reaction with a resist compound or the like. Most of the photoresists currently developed are chemically amplified.

As such acids are generated from a photoacid generator upon exposure to light, an alkane sulfonic acid, an alkane sulfonic acid in which some or all of the hydrogen atoms of the alkyl group of the alkane sulfonic acid are fully fluorinated, and the like are used.

A photoacid generator that generates an alkane sulfonic acid generally generates a weak acid. An alkane sulfonic acid has a problem in that the acid strength for the deprotection of a protective group in a resist compound, such as a tertiary ester group, is not sufficient, resulting in reduced sensitivity and degraded lithography performance, such as LWR.

Meanwhile, in the case of a photoacid generator that generates an alkane sulfonic acid in which all the hydrogen atoms of the alkyl group are fully fluorinated, the acid strength is sufficient for the deprotection reaction of a hard-to-deprotect protective group in a resist compound, and many such photoacid generators have been put to practical use. However, there has been a problem in that because the acid strength is too high, an unexpected reaction occurs during elimination reaction of the protective group for converting the dissolution contrast of the resist compound, resulting in the formation of foreign substances after development or at the time of resist stripping, for example.

Accordingly, in Patent Literature 1, it has been reported that the problem of the formation of foreign substances is solved using a known sulfonic acid having moderate acid strength, in which the hydrogen atoms of the alkyl group of an alkane sulfonic acid are partially substituted with a fluorine atom, a nitro group, or the like, which is an electron-withdrawing group. However, in a compound that generates a sulfonic acid having three or more fluorine atoms, foreign substances are formed after development or at the time of resist stripping, and satisfactory results have not yet been obtained.

In Patent Literature 2, it has been reported that when a compound that generates a sulfonic acid, in which an alkyl group and a perfluoroalkyl group are introduced into the α-carbon atoms of methanesulfonic acid, is used, the sulfonic acid has moderate acid strength without forming foreign substances. However, sufficient acid strength has not yet been obtained. In addition, Patent Literature 3 discloses a sulfonic acid having high acid strength, but sufficient characteristics have not yet been obtained regarding the formation of foreign substances.

CITATION LIST

Patent Literature

Patent Literature 1: JP 10-7650 A
Patent Literature 2: JP 2003-327572 A
Patent Literature 3: JP 2008-7410 A

BRIEF SUMMARY

Technical Problem

In terms of high sensitivity, it is preferable that the acid strength of a photoacid generator is high to some extent. However, meanwhile, for fine patterning, it is preferable that the acid diffusivity is low. That is, it has been demanded to satisfy both high acid strength and low acid diffusivity.

In light of these circumstances, an object of some aspects of this disclosure is to provide a sulfonic acid derivative that generates an acid having sufficient acid strength and also has low acid diffusivity. In addition, another object is to provide a sulfonic acid derivative, which, when used as a photoacid generator, has excellent fine resolution in lithography and also reduces line width roughness (LWR) in a fine pattern. In addition, another object is to provide a photoacid generator using the sulfonic acid derivative, a resist composition including the photoacid generator, and a method for producing a device using the resist composition.

Incidentally, prior to this disclosure, the applicants herein proposed a sulfonic acid derivative suitable as a photoacid generator and a photo-generating acid, which does not form foreign substances, generates an acid having sufficient acid strength, and is for use as a resist composition material (WO 2011/093139). This disclosure is an improvement of the invention described in WO 2011/093139, and provides provide a sulfonic acid derivative that has excellent resolution in lithography and further reduces line width roughness (LWR) in a fine pattern.

Solution to Problem

One aspect of this disclosure for solving the problem is a sulfonic acid derivative represented by the following general formula (1):

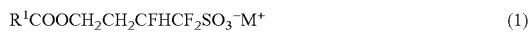

where:
  $R^1$ represents a monovalent organic group having carbon number of 1 to 200, having at least one hydroxyl group and optionally having a substituent other than the hydroxyl group; and $M^+$ represents a counter cation.

Another aspect of this disclosure is a photoacid generator including the above sulfonic acid derivative.

Another aspect of this disclosure is a resist composition including the above photoacid generator and a compound that reacts with an acid.

Another aspect of this disclosure is a method for producing a device, including: a resist film-forming step of forming a resist film by applying the above resist composition to a substrate; a photolithography step of exposing the above resist film to an active energy ray in a pattern shape; and a pattern-forming step of obtaining a photoresist pattern by developing an exposed resist film.

Advantageous Effects

A sulfonic acid derivative according to one aspect of this disclosure is useful as a photoacid generator that generates an acid having sufficient acid strength upon active energy ray irradiation. In addition, the sulfonic acid derivative according to one aspect of the disclosure is advantageous in that when used as a photoacid generator for a resist composition, it has excellent resolution in lithography and also reduces line width roughness (LWR) in a fine pattern.

DETAILED DESCRIPTION

Hereinafter, this disclosure will be described in detail.
1. Sulfonic Acid Derivative The sulfonic acid derivative according to one aspect of this disclosure is represented by the above general formula (1). Incidentally, "sulfonic acid derivative" refers to a sulfonic acid or a salt thereof. In addition, the sulfonic acid derivative represented by the above general formula (1) of this disclosure may be optically active or inactive.

The sulfonic acid derivative according to one aspect of the disclosure is a compound having a specific structure in which all the hydrogen atoms at the α-position and some of the hydrogen atoms at the β-position are substituted with fluorine atoms, where the group $R^1$ bound to a carbonyl group has at least one hydroxyl group. Because the sulfonic acid derivative has a specific structure having fluorine atoms, and the group $R^1$ has at least one hydroxyl group when used as a photoacid generator for a resist composition, it generates an acid having sufficient acid strength upon an active energy ray irradiation, has excellent resolution in lithography, and also reduces line width roughness (LWR) in a fine pattern.

In addition, because the group $R^1$ in the above general formula (1) has at least one hydroxyl group, in the case where the sulfonic acid derivative is used as a photoacid generator together with, for example, a base polymer having an acrylate structure, a hydroxyl group, or the like, due to the interaction, such as hydrogen bonding, between the base polymer and the sulfonic acid derivative, the acid diffusivity tends to decrease.

It is possible that substituents other than a hydroxyl group, such as an amino group and a cyano group, also affect the interaction such as hydrogen bonding. However, compared with them, a hydroxyl group has more remarkable effects in suppressing acid diffusivity for the following reasons. An amino group may deactivate the acid generated from a photoacid generator. A cyano group has a weaker polar interaction compared with a hydroxyl group. A cyano group may react with the generated acid and then change into a carboxyl group, and such carboxyl group has a small pKa. Thus, its interaction, such as hydrogen bonding, is weak in addition to a hydroxyl group.

A nitro group is not a proton-donating group, and thus its polar interaction with an acrylic resin or the like, which is generally used as a polymer for a resist, is likely to be weak.

In addition, a halogen atom is decomposed during exposure and may generate active halogen species. The generation of halogen species may cause damage to the exposure apparatus and thus is not preferable.

In the above general formula (1), $R^1$ represents a monovalent organic group having carbon number of 1 to 200, having at least one hydroxyl group and optionally having a substituent other than the hydroxyl group. Preferred examples of the organic group include a group having carbon number of 1 to 200 represented by the following formula (2).

In the above formula (2), $R^2$ is a monovalent group selected from the group consisting of: a linear, branched or cyclic aliphatic hydrocarbon group; an aromatic hydrocarbon group; and an aliphatic heterocyclic group or aromatic heterocyclic group containing, in the skeleton, at least one group selected from the group consisting of —O—, —CO—, —COO—, —OCO—, —O—CO—O—, —NHCO—, —CONH—, —NH—CO—O—, —O—CO—NH—, —NH—, —N=, —S—, —SO—, and —SO$_2$—.

In addition, A is each independently a direct bond, or a group selected from the group consisting of —O—, —CO—, —COO—, —OCO—, —O—CO—O—, —NHCO—, —CONH—, —NH—CO—O—, —O—CO—NH—, —NH—, —S— and —CO—O—CH$_2$—CO—O—.

$R^3$ is each independently a divalent group selected from the group consisting of: a linear, branched or cyclic aliphatic hydrocarbon group; an aromatic hydrocarbon group; and an aliphatic heterocyclic group or aromatic heterocyclic group containing, in the skeleton, at least one group selected from the group consisting of —O—, —CO—, —COO—, —OCO—, —O—CO—O—, —NHCO—, —CONH—, —NH—CO—O—, —O—CO—NH—, —NH—, —N=, —S—, —SO—, and —SO$_2$—.

In addition, n is an integer of 0 or 1 to 10; however, when n is 0, $R^2$ has the hydroxyl group, and when n is 1 or more, at least one of $R^2$ and $R^3$ has the hydroxyl group. n is preferably 0 to 5, and more preferably 0 to 3.

Incidentally, in the case where $R^1$ has a substituent, it is preferable that the number of carbon atoms is 1 to 200 including the number of carbon atoms in the substituent. The number of carbon atoms is more preferably 1 to 100, still more preferably 1 to 30, and particularly preferably 3 to 30. In addition, it is preferable that $R^1$ has a substituent. That is, it is preferable that at least one hydrogen in $R^2$ and $R^3$ is substituted with the substituent.

Examples of substituents that $R^1$ may have in addition to a hydroxyl group include, but are not limited to, a carboxyl group, an alkoxy group (—$OR^4$), an acyl group (—$COR^4$), an alkoxycarbonyl group (—$COOR^4$), an aryl group (—$Ar^1$), an aryloxy group (—$OAr^1$), a phosphino group, an alkylthio group (—$SR^4$), and an arylthio group (—$SAr^1$).

It is preferable that the above $R^4$ is an alkyl group of which the carbon number is equal to or more than 1. Specific preferred examples of the alkyl group of which the carbon number is equal to or more than 1 include: linear alkyl groups such as a methyl group, an ethyl group, an n-propyl group, an n-butyl group, an n-pentyl group, an n-hexyl group, an n-octyl group, and an n-decyl group; branched alkyl groups, such as an isopropyl group, an isobutyl group, a tert-butyl group, an isopentyl group, a tert-pentyl group, and a 2-ethylhexyl group; silyl-group-substituted alkyl groups having one hydrogen substituted with a trialkylsilyl group, such as a trimethylsilyl group, a triethylsilyl group, or a dimethylethylsilyl group; and alkyl groups having at least one hydrogen atom substituted with a cyano group or a halogen group.

It is preferable that $Ar^1$ in the substituent is an aryl group. Specific preferred examples of the aryl group as $Ar^1$ include a phenyl group, a biphenyl group, a terphenyl group, a quaterphenyl group, a naphthyl group, an anthryl group, a phenanthrenyl group, a pentalenyl group, an indenyl group, an indacenyl group, an acenaphtyl group, a fluorenyl group, a heptalenyl group, a naphthacenyl group, a pyrenyl group, a chrysenyl group, a tetracenyl group, a furanyl group, a thienyl group, a pyranyl group, a thiopyranyl group, a pyrrolyl group, an imidazoyl group, an oxazolyl group, a thiazolyl group, a pyrazoyl group, a pyridyl group, an isobenzofuranyl group, a benzofuranyl group, an isochromenyl group, a chromenyl group, an indolyl group, an isoindolyl group, a benzoimidazoyl group, a xanthenyl group, an acridinyl group, and a carbazoyl group.

$R^2$ in the above general formula (2) may have a substituent. Specific examples of unsubstituted linear or branched monovalent aliphatic hydrocarbon groups as $R^2$ include: alkyl groups such as a methyl group, an ethyl group, an n-propyl group, an i-propyl group, an n-butyl group, a t-butyl group, an n-pentyl group, an i-pentyl group, an n-hexyl group, an i-hexyl group, an n-octyl group, an i-octyl group, a 2-ethylhexyl group, and an n-dodecyl group; and alkenyl groups and alkynyl groups in which at least one carbon-carbon single bond of such an alkyl group is substituted with a carbon-carbon double bond or a carbon-carbon triple bond.

Examples of unsubstituted cyclic monovalent aliphatic hydrocarbon groups as $R^2$ in the above general formula (2) include a monocyclic aliphatic hydrocarbon group, a spirocyclic aliphatic hydrocarbon group, a bridged cyclic aliphatic hydrocarbon group, a fused polycyclic aliphatic hydrocarbon group, and a linked polycyclic aliphatic hydrocarbon group in which at least two of these groups are directly linked through a single bond or a linking group containing a double bond.

Examples of the above monocyclic aliphatic hydrocarbon group include a cyclopropyl group, a cyclopentyl group and a cyclohexyl group.

Examples of the above spirocyclic aliphatic hydrocarbon group include spiro[3,4]octane and spirobicyclopentane.

Examples of the above bridged cyclic aliphatic hydrocarbon group include those having a skeleton in which at least two monocyclic hydrocarbons are bridged, such as norbornane, tricyclodecane, tetracyclododecane and adamantane.

Examples of the above fused polycyclic aliphatic hydrocarbon group include decalin and groups having the following steroid skeleton.

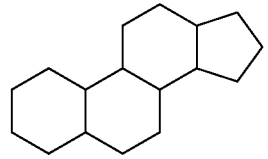

Chemical Formula 1

Examples of the above linked polycyclic aliphatic hydrocarbon group include groups having a bicyclohexane skeleton.

The above monovalent cyclic aliphatic hydrocarbon group may also be a group in which at least one carbon-carbon single bond is substituted with a carbon-carbon double bond or a carbon-carbon triple bond.

As examples of substituents for $R^2$ in the above general formula (2), those same as substituents for $R^1$ in the above general formula (1) can be mentioned.

As substituted linear, branched or cyclic monovalent aliphatic hydrocarbon groups as $R^2$ in the above general formula (2), the examples of unsubstituted monovalent aliphatic hydrocarbon groups described above, which have the above substituents, can be mentioned. Specific examples thereof include a benzyl group, a methoxymethyl group, a methylthiomethyl group, an ethoxymethyl group, a phenoxymethyl group, a methoxycarbonylmethyl group, an ethoxycarbonylmethyl group, an acetylmethyl group, a fluoromethyl group, a trifluoromethyl group, a chloromethyl group, a trichloromethyl group, a 2-fluoropropyl group, a trifluoroacetylmethyl group, a trichloroacetylmethyl group, a pentafluorobenzoylmethyl group, an aminomethyl group, a cyclohexylaminomethyl group, a diphenylphosphinomethyl group, a trimethylsilylmethyl group, a 2-phenylethyl group, a 3-phenylpropyl group and a 2-aminoethyl group.

Examples of monovalent aromatic hydrocarbon groups as $R^2$ in the above general formula (2) include a monocyclic aromatic hydrocarbon group, a fused polycyclic aromatic hydrocarbon group in which at least two monocyclic aromatic hydrocarbons are fused, and a linked polycyclic aromatic hydrocarbon group in which at least two monocyclic aromatic hydrocarbons are directly linked through a single bond or a linking group containing a double bond. These aromatic hydrocarbon groups may have the above substituents.

Examples of the above monocyclic aromatic hydrocarbon group include a group having a cyclopentene, benzene, or like skeleton.

Examples of the above fused polycyclic aromatic hydrocarbon group include a group having an indene, naphthalene, azulene, anthracene, phenanthrene, naphthacene, fluorine, or like skeleton.

Examples of the above linked polycyclic aromatic hydrocarbon group include a group having a biphenyl, terphenyl, stilbene, or like skeleton.

Examples of the monovalent aliphatic heterocyclic group as $R^2$ in the above general formula (2) include a group having an oxetane, cyclohexanone, acetidin-2-one, pyrrolidine, piperidine, piperazine, morpholine, quinuclidine, or like skeleton. In addition to them, the cyclic aliphatic hydrocarbon groups described above, in which at least one carbon atom is substituted with a heteroatom, can be mentioned. These aliphatic heterocyclic groups may have the above substituents.

In addition, the above monovalent aliphatic heterocyclic group may also be a group in which at least one a carbon-carbon single bond or a single bond between carbon and an atom other than carbon (heteroatom) is substituted with a double bond or a triple bond.

Examples of monovalent aromatic heterocyclic groups as $R^2$ in the above general formula (2) include a monocyclic aromatic heterocyclic group, a fused polycyclic aromatic heterocyclic group in which at least one monocyclic aromatic heterocycle is fused to the above aromatic hydrocarbon group or aromatic heterocyclic group, and a linked polycyclic aromatic heterocyclic group in which at least one monocyclic aromatic heterocycle and the above aromatic hydrocarbon group or aromatic heterocyclic group are directly linked through a single bond or a linking group containing a double bond. These aromatic heterocyclic groups may have the above substituents.

Examples of the above monocyclic aromatic heterocyclic group include a group having a furan, thiophene, pyrrole, imidazole, pyran, pyridine, pyrimidine, pyrazine, or like skeleton.

Examples of the above fused polycyclic aromatic heterocyclic group include a group having an indole, purine, quinoline, isoquinoline, chromene, chromone, coumarin, thianthrene, dibenzothiophene, phenothiazine, phenoxazine, xanthene, acridine, phenazine, carbazole, or like skeleton.

Examples of the above linked polycyclic aromatic heterocyclic group include 4-phenylpyridine, 9-phenylacridine and bathophenanthroline.

As the above $R^3$, the monovalent groups described above as examples of aliphatic hydrocarbon groups, aromatic hydrocarbon groups, aliphatic heterocyclic groups, and aromatic heterocyclic groups as $R^2$, of which valence is changed from 1 to 2, can be mentioned. Incidentally, when n is equal to or more than 2, $R^3$ can be each independently selected from the divalent group.

In terms of reducing the acid diffusivity, it is preferable that the above $R^2$ is a monovalent cyclic aliphatic hydrocarbon group, aromatic hydrocarbon group, or polycyclic group thereof. It is more preferable that $R^2$ is a spirocyclic aliphatic hydrocarbon group, a fused polycyclic aliphatic hydrocarbon group, a linked polycyclic aliphatic hydrocarbon group, a fused polycyclic aromatic hydrocarbon group, a linked polycyclic aromatic hydrocarbon group, or the like. For the same reason, $R^3$ is also preferably a divalent cyclic aliphatic hydrocarbon group, aromatic hydrocarbon group, or polycyclic group thereof.

Specific examples of $R^1$ in the above formula (1) include the structures shown below. Incidentally, in the following structural formulae, "*" represents "—$CH_2CH_2CFHCF_2SO_3^-M^+$" of $R^1COOCH_2CH_2CFHCF_2SO_3^-M^+$ in the above formula (1). That is, the following structural formulae each represent the structure of $R^1COO—$.

Incidentally, in the following structural formulae, the configuration is not limited to the following.

Chemical Formula 2

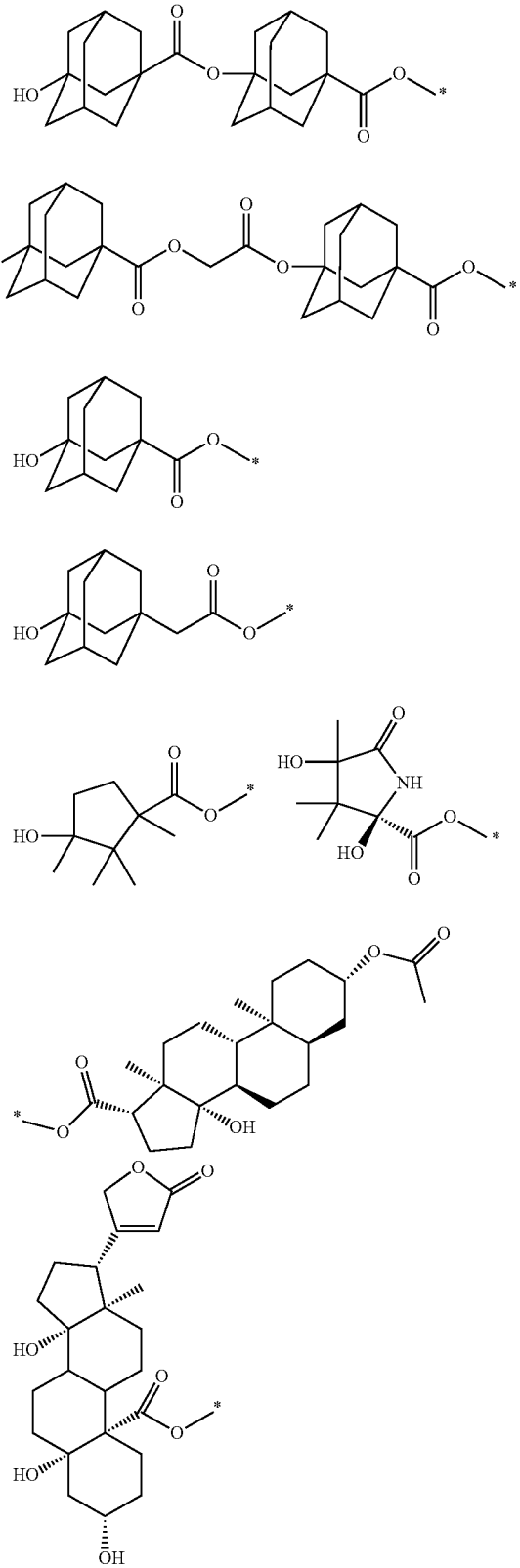

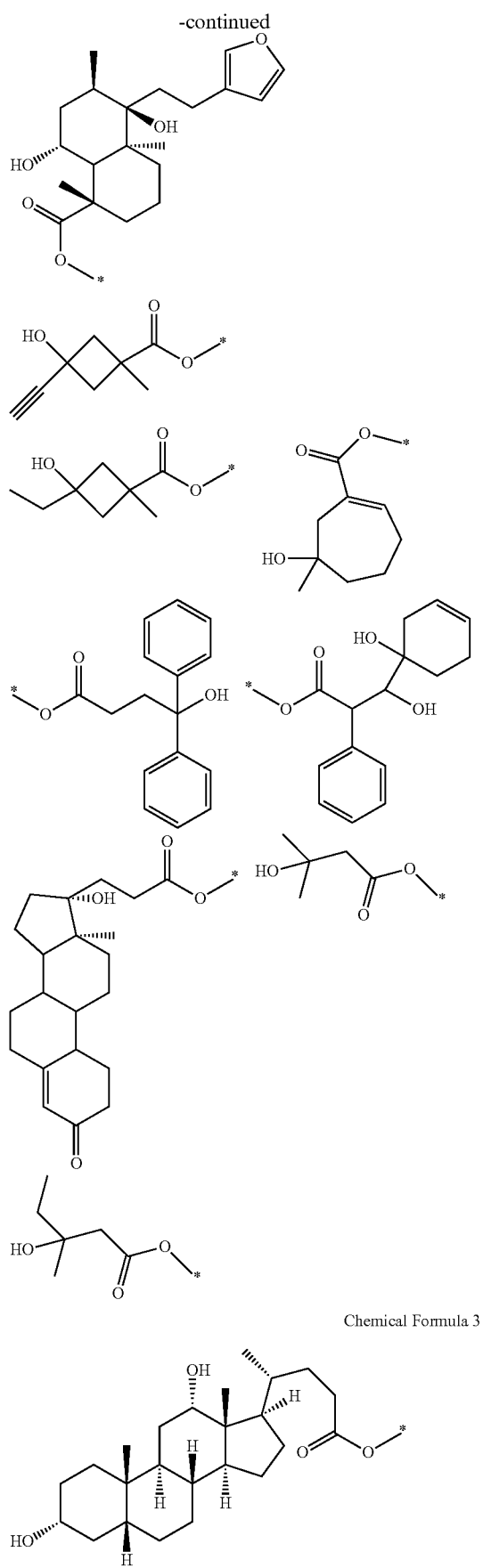
Chemical Formula 3
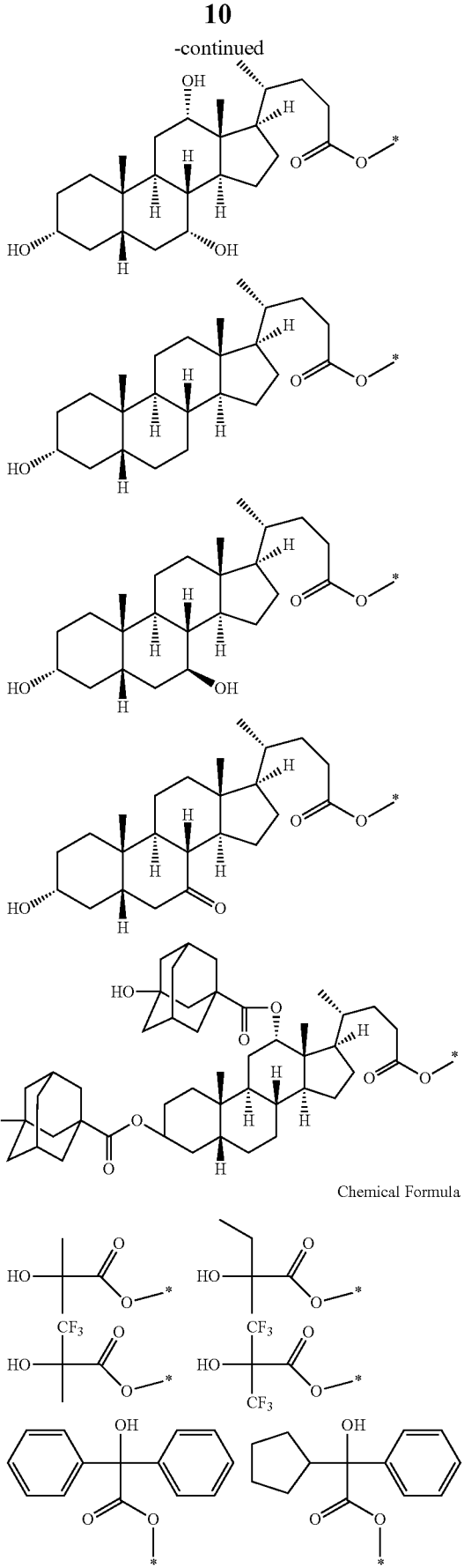
Chemical Formula 4

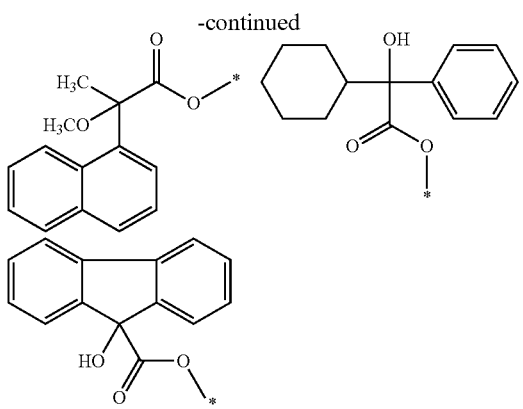

The number of hydroxyl groups introduced into the R¹ depends on the affinity with a base polymer when used as a photoacid generator. However, in terms of solubility, the number is preferably equal to or less than 10, more preferably 1 to 5, and still more preferably 1 to 3. In addition, in terms of reducing the acid diffusivity, it is preferable that the hydroxyl group is present on a hydrophobic group, such as the cyclic aliphatic hydrocarbon group or aromatic hydrocarbon group in R¹, for example.

Among the above compound examples, in terms of reducing the acid diffusivity, those having a hydroxyl group on the adamantane skeleton and those having a hydroxyl group on the steroid skeleton are preferable.

As a cation M⁺ to form a salt with a sulfonic acid, specifically, a hydrogen ion, a metal ion and an onium ion can be mentioned.

Specific examples of the metal ion, which is the cation M⁺, include a monovalent cation of first-group element, such as a lithium ion, a sodium ion and a potassium ion, a bivalent cation of second-group element, such as a magnesium(II) ion and a calcium(II) ion, a transition metal ion such as an iron(II) ion, an iron(III) ion, a copper(I) ion, a copper(II) ion, a nickel(II) ion and a nickel(III) ion, and heavy metal ions such as a lead(II) ion. These metal ions may form a complex with a ligand.

In addition, as the onium ion, which is the cation M⁺, an onium salt composed of a nitrogen atom, a sulfur atom, a halogen atom, a phosphorus atom, or the like can be mentioned. Specific examples thereof include an onium salt composed of a nitrogen atom, such as an ammonium ion, a methylammonium ion, a dimethylammonium ion, a trimethylammonium ion, a tetramethylammonium ion, a phenylammonium ion, a diphenylammonium ion, a triphenylammonium ion, a dimethylphenylammonium ion, a trimethylphenylammonium ion, a pyridinium ion, an alkylpyridinium ion, a fluoropyridinium ion, a chloropyridinium ion, a bromopyridinium ion, a tetramethylammonium ion, an imidazolium ion and a quinolinium ion, an onium salt composed of a sulfur atom, such as a trimethylsulfonium ion, a tributylsulfonium ion, a dimethyl(2-oxocyclohexyl)sulfonium ion, a bis(2-oxocyclohexyl)methylsulfonium ion, a (10-camphanoyl)methyl(2-oxocyclohexyl)sulfonium ion, a (2-norbornyl)methyl(2-oxocyclohexyl)sulfonium ion, a triphenylsulfonium ion, a diphenyltolylsulfonium ion, a diphenylxylyl sulfonium ion, a mesityldiphenylsulfonium ion, a (t-butylphenyl)diphenylsulfonium ion, an (octylphenyl)diphenylsulfonium ion, a (cyclohexylphenyl)diphenylsulfonium ion, a biphenyldiphenylsulfonium ion, a (hydroxymethylphenyl)diphenylsulfonium ion, a (methoxymethylphenyl)diphenylsulfonium ion, an (acetylphenyl)diphenylsulfonium ion, a (benzoylphenyl)diphenylsulfonium ion, a (hydroxycarbonylphenyl)diphenylsulfonium ion, a (methoxycarbonylphenyl)diphenylsulfonium ion, a (trifluoromethylphenyl)diphenylsulfonium ion, a (fluorophenyl)diphenylsulfonium ion, a (chlorophenyl)diphenylsulfonium ion, a (bromophenyl)diphenylsulfonium ion, an (iodophenyl)diphenylsulfonium ion, a pentafluorophenyldiphenylsulfonium ion, a (hydroxyphenyl)diphenylsulfonium ion, a (methoxyphenyl)diphenylsulfonium ion, a (butoxyphenyl)diphenylsulfonium ion, an (acetyloxyphenyl)diphenylsulfonium ion, a (benzoyloxyphenyl)diphenylsulfonium ion, a (dimethylcarbamoylphenyl)diphenylsulfonium ion, an (acetylamidophenyl)diphenylsulfonium ion, a phenylditolylsulfonium ion, a phenyldixylylsulfonium ion, a dimesitylphenylsulfonium ion, a bis(t-butylphenyl)phenylsulfonium ion, a bis(octylphenyl)phenylsulfonium ion, a bis(cyclohexylphenyl)phenylsulfonium ion, a dibiphenylphenylsulfonium ion, a bis(hydroxymethylphenyl)phenylsulfonium ion, a bis(methoxymethylphenyl)phenylsulfonium ion, a bis(acetylphenyl)phenylsulfonium ion, a bis(benzoylphenyl)phenylsulfonium ion, a bis(hydroxycarbonylphenyl)phenylsulfonium ion, a bis(methoxycarbonylphenyl)phenylsulfonium ion, a bis(trifluoromethylphenyl)phenylsulfonium ion, a bis(fluorophenyl)phenylsulfonium ion, a bis(chlorophenyl)phenylsulfonium ion, a bis(bromophenyl)phenylsulfonium ion, a bis(iodophenyl)phenylsulfonium ion, a dipentafluorophenylphenylsulfonium ion, a bis(hydroxyphenyl)phenylsulfonium ion, a bis(methoxyphenyl)phenylsulfonium ion, a bis(butoxyphenyl)phenylsulfonium ion, a bis(acetyloxyphenyl)phenylsulfonium ion, a bis(benzoyloxyphenyl)phenylsulfonium ion, a bis(dimethylcarbamoylphenyl)phenylsulfonium ion, a bis(acetylamidophenyl)phenylsulfonium ion, a tristolylsulfonium ion, a trisxylylsulfonium ion, a trismesitylphenylsulfonium ion, a tris(t-butylphenyl)sulfonium ion, a tris(octylphenyl)sulfonium ion, a tris(cyclohexylphenyl)sulfonium ion, a tribiphenylsulfonium ion, a tris(hydroxymethylphenyl)sulfonium ion, a tris(methoxymethylphenyl)sulfonium ion, a tris(acetylphenyl)sulfonium ion, a tris(benzoylphenyl)sulfonium ion, a tris(hydroxycarbonylphenyl)sulfonium ion, a tris(methoxycarbonylphenyl)sulfonium ion, a tris(trifluoromethylphenyl)sulfonium ion, a tris(fluorophenyl)sulfonium ion, a tris(chlorophenyl)sulfonium ion, a tris(bromophenyl)sulfonium ion, a tris(iodophenyl)sulfonium ion, a dipentafluorophenylsulfonium ion, a tris(hydroxyphenyl)sulfonium ion, a tris(methoxyphenyl)sulfonium ion, a tris(butoxyphenyl)sulfonium ion, a tris(acetyloxyphenyl)sulfonium ion, a tris(benzoyloxyphenyl)sulfonium ion, a tris(dimethylcarbamoylphenyl)sulfonium ion, a tris(acetylamidophenyl)sulfonium ion, a methyldiphenylsulfonium ion, an ethyldiphenylsulfonium ion, a butyldiphenylsulfonium ion, a hexyldiphenylsulfonium ion, an octyldiphenylsulfonium ion, a cyclohexyldiphenylsulfonium ion, a 2-oxocyclohexyldiphenylsulfonium ion, a norbornyldiphenylsulfonium ion, a camphanoyldiphenylsulfonium ion, a pinanoyldiphenylsulfonium ion, a naphthyldiphenylsulfonium ion, an anthranildiphenylsulfonium ion, a benzyldiphenylsulfonium ion, a trifluoromethyldiphenylsulfonium ion, a methoxycarbonylmethyldiphenylsulfonium ion, a butoxycarbonylmethyldiphenylsulfonium ion, a benzoylmethyldiphenylsulfonium ion, a (methylthiophenyl)diphenylsulfonium ion, a (phenylthiophenyl)diphenylsulfonium ion, an (acetylphenylthiophenyl)diphenylsulfonium ion, a dimethylphenylsulfonium ion, a diethylphenylsulfonium ion, a dibutylphenylsulfonium ion, a dihexylphenylsulfonium ion, a dioctylphenylsulfonium ion, a dicyclohexylphenylsulfonium ion, a bis(2-oxocyclohexyl)phenylsulfonium ion, a dinorbornylphenylsulfonium ion, a dicamphanoyl phenylsulfonium ion, a dipinanoylphenylsulfonium ion, a dinaphthylphenylsulfonium ion, a dibenzylphenylsulfonium ion, a trifluoromethyldiphenylsulfonium ion, a bis(methoxycarbonylmethyl)phenylsulfonium ion, a bis(butoxycarbonylmethyl)phenylsulfonium ion, a dibenzoylmethylphenylsulfonium ion, a bis(methylthiophenyl)phenylsulfonium ion, a bis(phenylthiophenyl)phenylsulfonium ion, a bis(acetylphenylthiophenyl)phenylsulfonium ion, a dimethyl(2-oxocyclohexyl)sulfonium ion, a bis(2-oxocyclohexyl)methylsulfonium ion, a (10-camphanoyl)methyl(2-oxocyclohexyl)sulfonium ion, a (2-norbornyl)methyl(2-oxocyclohexyl)sulfonium ion, a trimethylsulfonium ion, a triethylsulfonium ion, a tributylsulfonium ion, a dihexylmethyl sulfonium ion, a trioctylsulfonium ion, a dicyclohexylethylsulfonium ion, a methyltetrahydrothiophenium ion, a methyltetrahydrothiophenium ion, a triphenyloxosulfonium ion and a bis[4-(diphenylsulfonio)phenyl]sulfide-bis ion, and an onium salt composed of a phosphorus atom, such as a tetraphenylphosphonium ion. Examples of a halonium salt include a diphenyliodonium ion, a bis-(t-butylphenyl)iodonium cation, a (methoxyphenyl)phenyliodonium ion, a (butoxyphenyl)phenyliodonium ion, a trifluoroethylphenyliodonium ion and a pentafluorophenylphenyliodonium ion. A sulfonium ion and an iodonium ion are preferable.

The sulfonic acid derivative represented by the above general formula (1) is a compound having a specific structure in which all the hydrogen atoms at the α-position and some of the hydrogen atoms at the β-position are fluorine-substituted. In the case where the sulfonic acid derivative is used as a photoacid generator, it is preferable that a cation is a sulfonium ion or an iodonium ion. In the sulfonic acid derivative represented by the above general formula (1), a fluorine atom is present at specific positions, and the cation is a sulfonium ion or an iodonium ion. As a result, the sulfonic acid derivative is useful as a photoacid generator that is efficiently decomposed by active energy ray irradiation, such as with KrF excimer laser light, ArF excimer laser light, $F_2$ excimer laser light, electron beams, X-rays, or EUV, and generates an acid having sufficient acid strength. In addition, the group $R^1$ bound to a carbonyl group has at least one hydroxyl group, whereby the acid diffusivity decreases. Accordingly, when used as a photoacid generator for a resist composition, the sulfonic acid derivative is advantageous in that it has excellent resolution in lithography and also reduces line width roughness (LWR) in a fine pattern.

In addition, when used as a photoacid generator for a resist composition, because of the presence of a hydroxyl group, the sulfonic acid derivative has high affinity with an alkali developing solution, resulting in an advantage in that foreign substances are unlikely to be formed after development or at the time of resist stripping.

Here, the sulfonic acid derivative of Patent Literature 3 described above is a compound having four fluorines, in which all the hydrogen atoms at the α-position and the β-position are fluorine-substituted. Accordingly, the acid strength is too high, and foreign substances tend to be formed after development, particularly after alkali development, or at the time of resist stripping. Incidentally, Patent Literature 3 does not have the idea of the sulfonic acid derivative represented by the above general formula (1) of this disclosure, in which all the hydrogen atoms at the α-position and some of the hydrogen atoms at the β-position are fluorine-substituted. Further, based on the production method described in Patent Literature 3, even when the raw materials are changed, for example, the sulfonic acid derivative according to one aspect of the disclosure cannot be produced. In addition, a sulfonic acid derivative having two fluorines at the α-position or the like does not have sufficient acid strength.

Generally, in a sulfonic acid derivative having three or more fluorine atoms, there usually is a problem in that foreign substances are formed after alkali development or at the time of resist stripping. Although the sulfonic acid derivative in one aspect of this disclosure has three fluorine atoms, because of the specific structure represented by above general formula (1), the acid strength is sufficient, and also almost no foreign substances are formed after development or at the time of resist stripping.

This disclosure is not limited to water-based development using an alkali developing solution, and is also applicable to water-based development using a neutral developing solution or organic solvent development using an organic solvent developing solution.

2. Photoacid Generator and Resist Composition Using the Same

In one aspect, this disclosure provides a photoacid generator containing the above sulfonic acid derivative (hereinafter sometimes referred to as "component (A)").

One aspect of the photoacid generator of the disclosure has the property of releasing an acid upon the active energy ray irradiation described above, and is capable of acting on an acid-reactive organic substance to cause decomposition or polymerization. Therefore, the sulfonic acid derivative according to one aspect of this disclosure can be preferably used as a photoacid generator for a positive-type or negative-type resist composition.

In one aspect, the disclosure provides a resist composition containing the above sulfonic acid derivative (component (A)) as a photoacid generator and a compound that reacts with an acid (hereinafter sometimes referred to as "component (B)").

Examples of a compound that react with an acid (component (B)) include a compound having an acid-dissociable group (hereinafter sometimes referred to as "component (B1)"), a compound having a polymerizable group that is polymerized by an acid (hereinafter sometimes referred to as "component (B2)"), and a cross-linking agent having a cross-linking effect caused by an acid (hereinafter sometimes referred to as "component (B3)").

The compound having an acid-dissociable group (component (B1)) is a compound from which an acid-dissociable group is dissociated by an acid to form a polar group, whereby its solubility in a developing solution changes. For example, in the case of water-based development using an alkali developing solution or the like, the compound is as follows: although the compound is insoluble in an alkali developing solution, due to an acid generated from the photoacid generator upon exposure, the acid-dissociable group is dissociated in the exposed position, whereby the compound turns soluble in an alkali developing solution.

In this disclosure, the developing solution is not limited to an alkali developing solution, and may also be a neutral developing solution or organic solvent development. Therefore, in the case of using an organic solvent developing solution, the compound having an acid-dissociable group is as follows: due to an acid generated from the photoacid generator upon exposure, the acid-dissociable group is deprotected in the exposed position, whereby the solubility of the compound in an organic solvent developing solution decreases.

Specific examples of a polar group include a carboxyl group, a hydroxyl group, an amino group, and a sulfo group (—SO$_3$H). Among them, a carboxyl group and a hydroxyl group are preferable.

The acid-dissociable group is a group in which a hydrogen atom of the polar group is protected by a protective group. The protective group is not particularly limited as long as it is a group usually used as an acid-dissociable group in the chemically amplified resist field, and specific examples thereof include a tertiary alkyl ester group, an acetal group, a tetrahydropyranyl group, a siloxy group, and a benzyloxy group.

The compound having an acid-dissociable group may be a low-molecular-weight compound, a polymer component, or a mixed component thereof. In the disclosure, a low-molecular-weight compound is a compound having a weight average molecular weight of less than 2,000, and a polymer component is a component having a weight average molecular weight of 2,000 or more. As the compound having an acid-dissociable group, a compound having a hydroxystyrene, methacrylate, or acrylate skeleton, in which the acid-dissociable group is pendant, for example, is suitably used.

When the compound having an acid-dissociable group (component (B1)) is a polymer component, it may also serve as a base polymer of the resist composition.

When the compound having an acid-dissociable group (component (B1)) is a polymer component, it is preferable that the polymer component has an acid-dissociable-group-containing unit. It is preferable that the polymer component contains units other than an acid-dissociable-group-containing unit. The units other than an acid-dissociable-group-containing unit are not particularly limited as long as they are units usually used in the chemically amplified resist field. Examples thereof include: a unit having at least one skeleton selected from the group consisting of a lactone skeleton, a sultone skeleton, and a lactam skeleton; and a unit having at least one group selected from the group consisting of an ether group, an ester group, a hydroxyl group, a glycidyl group and an oxetanyl group.

In this disclosure, as the compound having an acid-dissociable group (component (B1)), the compounds shown below can be mentioned, for example. However, the proportion of each unit and the structure of each unit are not limited thereto.

Chemical Formula 5

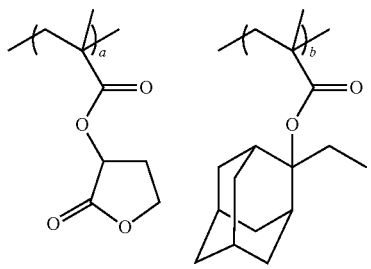

-continued

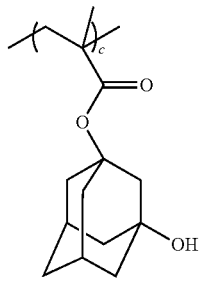

(a = 0.2, b = 0.3, c = 0.5, Mw = 9,300)

The compound having a polymerizable group that is polymerized by an acid (component (B2)) is a compound of which the polymerizable group is polymerized by an acid, whereby its solubility in a developing solution changes. For example, in the case of water-based development, the compound is as follows: although the compound is soluble in a water-based developing solution, due to an acid generated from the photoacid generator upon exposure, the polymerizable group is polymerized in the exposed position, whereby its solubility in a water-based developing solution decreases. Also in this case, the water-based developing solution may be replaced with an organic solvent developing solution.

Examples of a polymerizable group that are polymerized by an acid include an epoxy group, an acetal group, and an oxetanyl group. As the compound having the polymerizable group (component (B2)), a compound having a styrene skeleton, methacrylate, or acrylate skeleton having a polymerizable group, for example, is suitably used.

The compound having a polymerizable group that is polymerized by an acid (component (B2)) may be a polymerizable low-molecular-weight compound or may also be a polymerizable polymer component. When the compound having a polymerizable group that is polymerized by an acid is a polymer component, it may also serve as a base polymer of the resist composition.

The cross-linking agent having a cross-linking effect caused by an acid (component (B3)) is a compound that causes cross-linking with an acid to change solubility in a developing solution. For example, in the case of water-based development, the cross-linking agent acts on a compound soluble in a water-based developing solution and, after cross-linking, reduces the solubility of the compound in a water-based developing solution. Specifically, a cross-linking agent having an epoxy group, an acetal group, an oxetanyl group, or the like can be mentioned. At this time, as a compound to be cross-linked with, a compound having a phenolic hydroxyl group can be mentioned, for example.

The compound having a cross-linking effect caused by an acid (component (B3)) may be a polymerizable low-molecular-weight compound or may also be a polymerizable polymer component. When the compound having a cross-linking effect caused by an acid is a polymer component, it may also serve as a base polymer of the resist composition.

As a resist composition according to one aspect of this disclosure, more specifically, the following compositions can be mentioned, for example.

A resist composition including: the compound having an acid-dissociable group and the photoacid generator; a resist composition including the compound having a polymerizable group that is polymerized by an acid and the photoacid generator; a resist composition including a cross-linking agent having a cross-linking effect caused by an acid, a compound of which solubility in a developing solution changes as a result of reaction with the cross-linking agent, and the photoacid generator; and the like can be mentioned.

In the resist composition according to one aspect of the disclosure, the content of a photoacid generator (component (A)) is preferably 1 to 50 parts by mass, more preferably 1 to 30 parts by mass, and still more preferably 1 to 15 parts by mass, relative to 100 parts by mass of the resist composition component excluding the photoacid generator. When the photoacid generator is contained in the resist composition within the above range, for example, even when it is used for a permanent film, such as an insulating film in a display body or the like, the light transmission can be made high.

As necessary, the resist composition according to one aspect of this disclosure may further include, in addition to the above components, as optional components, a fluorine-containing water-repellent polymer or silicon-containing water-repellent polymer used in an ordinary resist composition (hereinafter sometimes referred to as "component (C)"), an organic solvent (hereinafter sometimes referred to as "component (D)"), an additive (hereinafter sometimes referred to as "component (E)"), and further other photoacid generators in combination.

As the water-repellent polymer (component (C)), a polymer that is usually used in an immersion exposure process can be mentioned. It is preferable that the water-repellent polymer has a higher fluorine atom or silicon atom content than the base polymer. As a result, in the case where a resist film is formed using the resist composition, the surface free energy of the water-repellent polymer is relatively lower than the surface free energy of the base resist, whereby the water-repellent polymer can be unevenly distributed on the resist film surface. Because of this effect, the tracking and retention of immersion water on the surface of the resist film are prevented, whereby the occurrence of defects is suppressed. At the same time, it becomes possible to reduce the amount of elution from the resist component to the immersion water, whereby lens contamination can be prevented.

The amount of component (C) in the resist composition is preferably 0.1 to 30 parts by mass, more preferably 1 to 20 parts by mass, and most preferably 1 to 10 parts by mass, relative to 100 parts by mass of the component (B).

The component (D) is not particularly limited as long as it is an organic solvent usually used in a resist composition.

As the component (E), various additives such as a quencher, an acidic compound, a dissolution inhibitor, a stabilizer, and a dye can be mentioned, and those usually used in a resist composition can be used.

3. Synthesis Method for Sulfonic Acid Derivative

The sulfonic acid derivative represented by the above general formula (1) can be synthesized through the following reaction paths, for example. First, 4-bromo-1,1,2-trifluoro-1-butene, which is a starting material, is acetylated with sodium acetate, then hydrolyzed with a base or the like, and further sulfonated with a bisulfite, thereby obtaining a sulfonate. Then, in a usual manner, the salt is salt-exchanged with the $M^+$ described above. Subsequently, the product is further esterified with an acid anhydride or acid halide having the above $R^1$, or condensed with a carboxylic acid having the above $R^1$, whereby the sulfonic acid derivative represented by the above general formula (1) can be obtained.

By suitably adjusting the esterification conditions, any of various groups illustrated above can be introduced as $R^1$ having at least one hydroxyl group into a 1,1,2-trifluoro-4-hydroxybutanesulfonate salt.

As an acid anhydride, acid halide, carboxylic acid, or the like having the above $R^1$, which serves as a raw material for the synthesis of a sulfonic acid derivative, an available product is used. Alternatively, it is also possible to prepare a corresponding raw material, suitably performing synthesis according to an ordinary method, and using the obtained product.

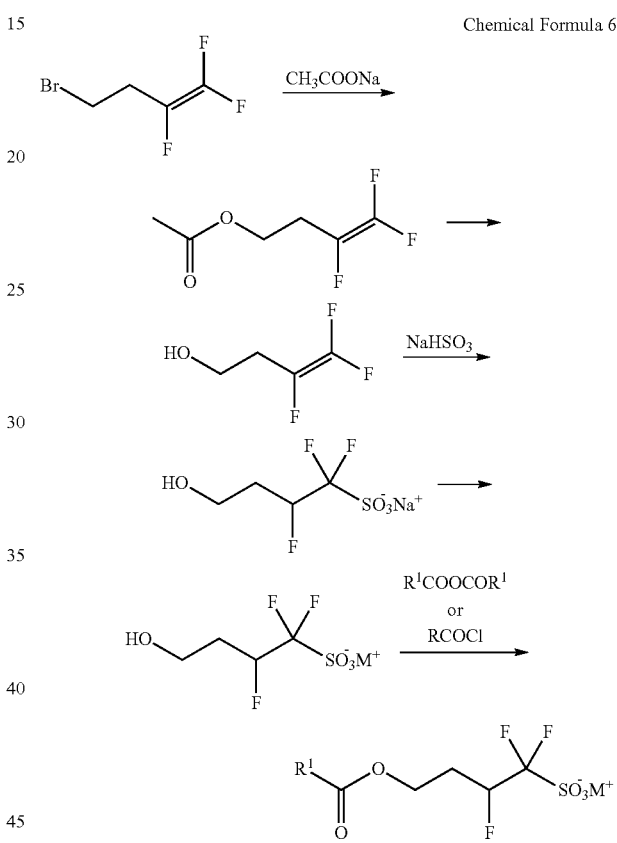

Chemical Formula 6

4. Method for Producing Device

In one aspect, this disclosure provides a method for producing a device, including: a resist film-forming step of forming a resist film by applying the resist composition to a substrate to form a resist film; a photolithography step of exposing the resist film to an active energy ray in a pattern shape; and a pattern-forming step of obtaining a photoresist pattern by developing an exposed resist film.

An active energy ray for use in exposure in the photolithography step may be any light as long as the sulfonic acid derivative of the disclosure is activated to generate an acid. Examples thereof include KrF excimer laser light, ArF excimer laser light, $F_2$ excimer laser light, electron beams, UV, visible light, X-rays, electron beams, ionic beams, i-rays, and EUV.

Other than the use of a resist composition containing the photoacid generator, the method may follow an ordinary method for producing a device.

EXAMPLES

Hereinafter, the disclosure will be described based on examples, but the disclosure is not limited to these examples.

Example 1

Synthesis of Sulfonic Acid Derivative

Example 1-1

Synthesis of sodium 1,1,2-trifluoro-4-hydroxybutanesulfonate

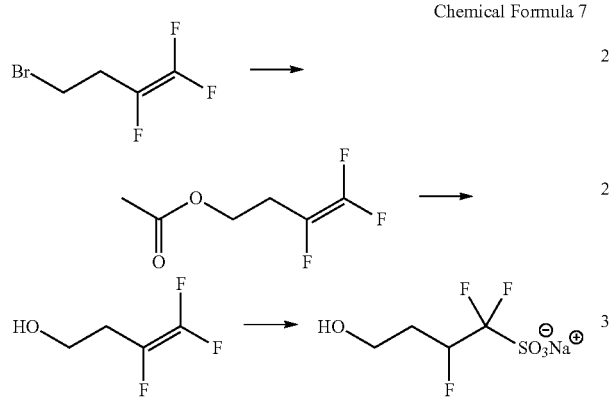

Chemical Formula 7

First Step 36.9 g of 4-bromo-1,1,2-trifluoro-1-butene and 65.4 g of sodium acetate are dissolved in 156.5 g of acetate and heated to 115° C. After stirring for 40 hours, the reaction mixture is cooled to 90° C., and 626 g of distilled water is added. Subsequently, the mixture is cooled to room temperature and extracted twice using 128 g of t-butyl methyl ether. Next, washing is performed using 165 g of an aqueous sodium carbonate solution to remove the residual acid. Subsequently, the solvent is distilled off on a rotary evaporator, thereby giving 25.6 g of 4-acetoxy-1,1,2-trifluoro-1-butene in a crude state. The results of the 1H-NMR measurement of this substance are indicated below.

1H-NMR (400 MHz, CDCl$_3$) δ 2.07 (s, 3H), 2.63 (d, t, d, d, 2H), 4.24 (t, 2H)

Second Step 25.0 g of 4-acetoxy-1,1,2-trifluoro-1-butene and 40.3 g of potassium carbonate are dissolved in a mixed solution of 49 g of methanol and 49 g of distilled water. The mixture is stirred at room temperature for 15 hours, and then the precipitated solid resulting from the reaction is removed by filtration. Then, the object substance is extracted with dichloromethane and subsequently purified by distillation, thereby giving 13.8 g of 3,4,4-trifluoro-3-buten-1-ol. The results of the 1H-NMR measurement of this substance are indicated below.

1H-NMR (400 MHz, CDCl$_3$) δ2.2 (s, 1H), 2.55 (d, t, d, d, 2H), 3.83 (t, 2H)

Third Step 11.9 g of 3,4,4-trifluoro-3-buten-1-ol, 29.5 g of sodium bisulfate, and 14.3 g of sodium sulfite are dissolved in 214 g of distilled water, and subsequently the mixture is heated to 90° C. After stirring for 15 hours, the reaction mixture is cooled to 25° C. or less. Next, the aqueous layer is washed with 24 g of toluene. Subsequently, the solvent is distilled off on a rotary evaporator, thereby giving 18.46 g of sodium 1,1,2-trifluoro-4-hydroxybutanesulfonate. From the results of 1H-NMR and ion chromatography measurements, this compound is confirmed to be an object substance. The 1H-NMR measurement results are indicated below.

1H-NMR (400 MHz, CDCl$_3$) δ1.9-2.4 (m, 2H), 3.5-3.7 (m, 2H), 4.9-5.2 (m, 1H)

Example 1-2

Synthesis of triphenylsulfonium 4-(3-hydroxyadamanthylcarbonyloxy)-1,1,2-trifluorobutanesulfonate

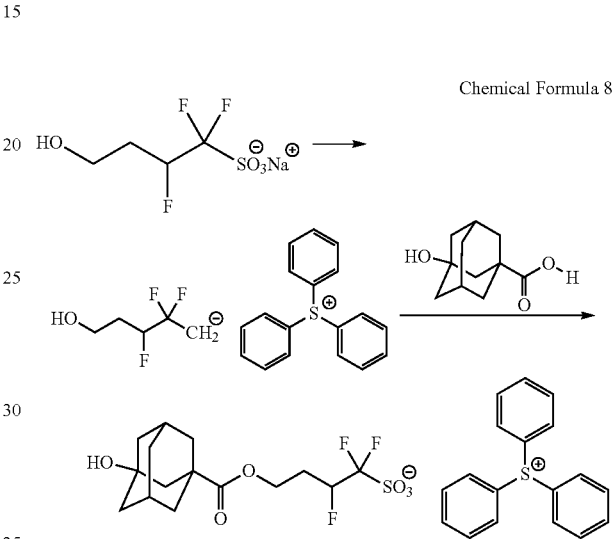

Chemical Formula 8

First Step 17.6 g of sodium 1,1,2-trifluoro-4-hydroxybutanesulfonate and 34.4 g of triphenylsulfonium methanesulfonate are added to a mixed solution of 106 g of water and 360 g of dichloromethane and stirred for 3 hours. After the reaction mixture is separated into two layers, the solvent in the organic layer is distilled off on a rotary evaporator, thereby giving 32.4 g of triphenylsulfonium 1,1,2-trifluoro-4-hydroxybutanesulfonate. The results of the 1H-NMR measurement of this substance are indicated below.

1H-NMR (400 MHz, CDCl$_3$) δ1.9-2.4 (m, 2H), 3.5-3.7 (m, 2H), 4.9-5.2 (m, 1H), 7.66-7.80 (m, 15H)

Second Step 9.4 g of triphenylsulfonium 1,1,2-trifluoro-4-hydroxybutanesulfonate and 4.3 g of 3-hydroxy-1-adamantanecarboxylic acid are added to 94.0 g of dichloromethane and 0.3 g of 4-dimethylaminopyridine and stirred. Subsequently, 5.5 g of 1-ethyl-3-(3-dimethylaminopropyl)carbodiimide hydrochloride is added at 15° C. or less and heated to 23° C. After stirring for 18 hours, the reaction mixture is cooled to 15° C. or less, and 10 mass % hydrochloric acid is added to halt the reaction. Then, the organic layer is washed with pure water. Subsequently, the solvent is distilled off on a rotary evaporator, thereby giving 7.1 g of triphenylsulfonium 4-(3-hydroxyadamanthylcarbonyloxy)-1,1,2-trifluorobutanesulfonate. The results of the 1H-NMR measurement of this compound are indicated below.

1H-NMR (400 MHz, DMSO-d6) δ1.47-1.65 (m, 12H), 1.82-2.11 (m, 1H), 2.18 (brs, 2H), 2.28-2.45 (m, 1H), 4.03-4.22 (m, 2H), 4.55 (s, 1H), 4.87-5.07 (m, 1H), 7.76-7.88 (m, 15H) The pKa of the obtained compound is calculated using ACD/Labs v.11.02. The results are indicated in Table 1.

Example 2

Synthesis of Sulfonic Acid Derivative

Synthesis is performed according to the same formulation as in Example 1-2 of Example 1 above, except for using β-hydroxy isovaleric acid in place of 3-hydroxy-1-adamantanecarboxylic acid, thereby synthesizing a sulfonic acid derivative represented by the following formula. 1H-NMR is performed to confirm that this compound is a target compound. The 1H-NMR measurement results are indicated below.

1H-NMR (400 MHz, DMSO-d6) δ1.47 (s, 6H), 1.80-2.10 (m, 1H), 2.28-2.47 (m, 3H), 4.05-4.24 (m, 2H), 4.50 (s, 1H), 4.87-5.05 (m, 1H), 7.79-7.92 (m, 15H)

Chemical Formula 9

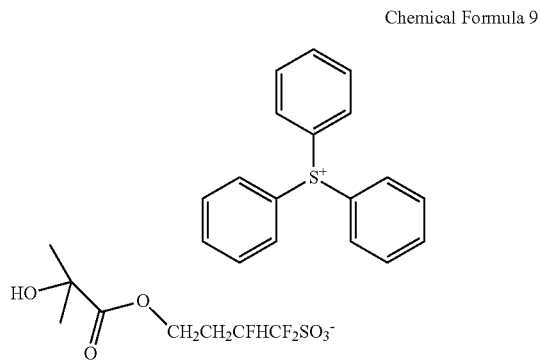

Example 3

Preparation of Photoresist Composition and Evaluation of Characteristics

Chemical Formula 10

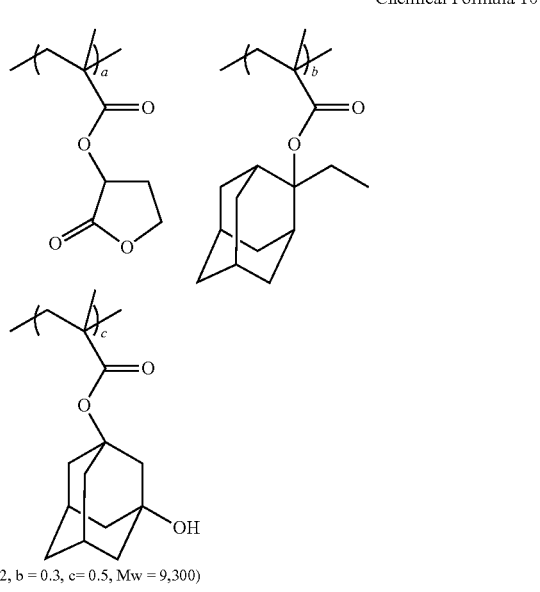

(a= 0.2, b = 0.3, c= 0.5, Mw = 9,300)

Five parts by mass of triphenylsulfonium 4-(3-hydroxyadamanthylcarbonyloxy)-1,1,2-trifluorobutanesulfonate synthesized above, 100 parts by mass of a polymer having a structural unit represented by the above general formula (3), and 0.2 parts by mass of triethanolamine are dissolved in 1,250 parts by mass of propylene glycol monomethyl ether acetate, and the mixture is filtered through a PTFE filter to prepare a photoresist composition solution. Next, the photoresist composition solution is applied to a silicon wafer by spin-coating and then pre-baked on a hot plate at 110° C. for 60 seconds to obtain a resist film having a thickness of 300 nm. The film is exposed using an ArF excimer laser stepper (wavelength: 193 nm) and then post-baked at 110° C. for 60 seconds. Subsequently, development is performed for 60 seconds in an aqueous solution of 2.38 mass % tetramethylammonium hydroxide, followed by rinsing with pure water for 30 seconds.

With respect to the obtained excellent pattern, the pattern surface after exposure and the silicon substrate surface after stripping were observed. As a result, there were no foreign substances. Incidentally, foreign substances are observed using a surface defect observation apparatus manufactured by KLA-Tencor Corporation (Model No.: KLA2351).

Resolution and line width roughness (LWR) are evaluated as follows. Using the resist composition prepared below in Comparative Example 2, the resolution and LWR are measured. Taking each value as 1, relative values of the resolution and LWR of triphenylsulfonium 4-(3-hydroxyadamanthylcarbonyloxy)-1,1,2-trifluorobutanesulfonate are calculated. The results are indicated in Table 1.

Example 4

A resist composition is prepared and evaluated in the same manner as in Example 3, except that 4.4 parts by mass of a sulfonic acid derivative synthesized in Examples 1-2 was used in place of 5 parts by mass of triphenylsulfonium 4-(3-hydroxyadamanthylcarbonyloxy)-1,1,2trifluorobutanesulfonate. As in Example 3, the pKa of the compound and the evaluation results of the resolution and LWR of the resist composition are indicated in Table 1.

Comparative Example 1

A resist composition is prepared and evaluated in the same manner as in Example 3, using 4.3 parts by mass of a sulfonic acid derivative represented by the following formula in place of 5 parts by mass of triphenylsulfonium 4-(3-hydroxyadamanthylcarbonyloxy)-1,1,2-trifluorobutanesulfonate. As in Example 3, the pKa of the compound and the evaluation results of the resolution and LWR of the resist composition are indicated in Table 1.

Chemical Formula 11

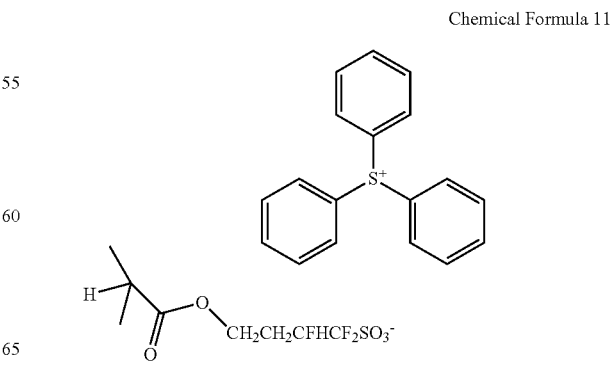

Comparative Example 2

A resist composition is prepared and evaluation performed in the same manner as in Example 1, using 4.3 parts by mass of a sulfonic acid derivative represented by the following formula in place of 5 parts by mass of triphenylsulfonium 4-(3-hydroxyadamanthylcarbonyloxy)-1,1,2-trifluorobutanesulfonate. The pKa of the compound is calculated in the same manner as in Example 3. In addition, the resolution and LWR of the resist composition in Comparative Example 2 are used as standards. The results are indicated in Table 1.

Chemical Formula 12

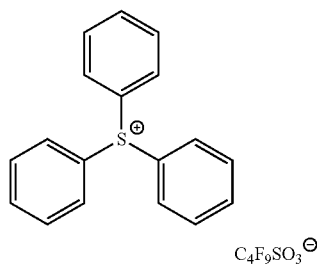

TABLE 1

|  | Example 3 | Example 4 | Comparative Example 1 | Comparative Example 2 |
|---|---|---|---|---|
| pKa | −2.8 | −2.8 | −2.8 | −3.6 |
| Resolution (Rel.) | 0.70 | 0.90 | 0.95 | 1 |
| LWR (Rel.) | 0.65 | 0.85 | 0.90 | 1 |

The resolution and LWR in Table 1 indicate that the smaller the values, the higher the effects.

From the above results, it can be seen that the sulfonic acid derivative of this disclosure has low acid diffusivity while maintaining the high acid strength, and thus is advantageous in that it has excellent resolution in lithography and also reduces LWR in a fine pattern.

INDUSTRIAL APPLICABILITY

A sulfonic acid derivative according to one aspect of the the disclosure generates an acid having sufficient acid strength upon an active energy ray irradiation and, thus, is useful as a photoacid generator for a resist composition. In addition, when the photoacid generator is used in a resist composition, there are advantages in that it forms almost no foreign substances after development or at the time of resist stripping, has excellent resolution in lithography, and also reduces line width roughness (LWR) in a fine pattern.

The invention claimed is:

1. A sulfonic acid derivative, wherein the sulfonic acid derivative is represented by the. following general formula (1):

$$R^1COOCH_2CH_2CFHCF_2SO_3^-M^+ \quad (1)$$

where:
R$^1$ represents a monovalent organic group having carbon number of 1 to 200, having at least one hydroxyl group and optionally having a substituent other than the hydroxyl group; and
M$^+$ represents a counter cation.

2. The sulfonic acid derivative according to claim 1, wherein the organic group is represented by the following formula (2):

$$R^2\text{-}(A\text{-}R^3)_n\text{---} \quad (2)$$

where:
R$^2$ is a monovalent group selected from the group consisting of: a linear, branched, or cyclic aliphatic hydrocarbon group; an aromatic hydrocarbon group; and an aliphatic heterocyclic group or aromatic heterocyclic group containing, in the skeleton, at least one group selected from the group consisting of —O—, —CO—, —COO—, —OCO—, —O—CO—O—, —NHCO—, —CONH—, —NH—CO—O—, —O—CO—NH—, —NH—, —N═, —S—, —SO—, and —SO$_2$—;
A is each independently a direct bond, or a group selected from the group consisting of —O—, —CO—, —COO—, —OCO—, —O—CO—O—, —NHCO—, —CONH—, —NH—CO—O—, —O—CO—NH—, —NH—, —S—, and —CO—O—CH$_2$—CO—O—;
R$^3$ is each independently a divalent group selected from the group consisting of: a linear, branched, or cyclic aliphatic hydrocarbon group; an aromatic hydrocarbon group; and an aliphatic heterocyclic group or aromatic heterocyclic group containing, in the skeleton, at least one group selected from the group consisting of —O—, —CO—, —COO—, —OCO—, —O—CO—O—, —NHCO—, —CONH—, —NH—CO—O—, —O—CO—NH—, —NH—, —N═, —S—, —SO—, and —SO$_2$—; and
n is an integer of 0 or 1 to 10, with the proviso that when n is 0, R$^2$ has the hydroxyl group, and when n is from 1 to 10, at least one of R$^2$ and R$^3$ has the hydroxyl group.

3. The sulfonic acid derivative according to claim 1, wherein the M$^+$ is a hydrogen ion, a metal ion, or an onium ion.

4. A photoacid generator composing:
a sulfonic acid derivative of the following general formula (1):

$$R^1COOCH_2CH_2CFHCF_2SO_3^-M^+ \quad (1)$$

wherein:
R$^1$ represents a monovalent organic group having carbon number of 1 to 200, having at least one hydroxyl group and optionally having a substituent other than the hydroxyl group; and
M$^+$ represents a counter cation.

5. A resist composition comprising:
the photoacid generator according to claim 4, and
a compound that reacts with an acid.

6. A method for producing a device, the method comprising:
a resist film-forming step of forming a resist film by applying the resist composition according to claim 5 to a substrate to form a resist film;
a photolithography step of exposing the resist film to an active energy ray in a pattern shape; and
a pattern-forming step of obtaining a photoresist pattern by developing a exposed resist film.

7. The sulfonic acid derivative of claim 2, wherein M$^+$ is selected from the group consisting of a hydrogen ion, a metal ion, and an onium ion.

8. The photoacid generator of claim 4, wherein the organic group is represented by the following formula (2):

$$R^2\text{-}(A\text{-}R^3)_n\text{---} \quad (2)$$

wherein:
- $R^2$ is a monovalent group selected from the group consisting of a linear, branched, or cyclic aliphatic hydrocarbon group; an aromatic hydrocarbon group; and an aliphatic heterocyclic group or aromatic heterocyclic group containing, in the skeleton, at least one group selected from the group consisting of —O—, —CO—, —COO—, —OCO—, —O—CO—O—, —NHCO—, —CONH—, —NH—CO—O—, —O—CO—NH—, —NH—, —N=, —S—, —SO—, and —SO$_2$—;
- A is each independently a direct bond, or a group selected from the group consisting of —O—, —CO—, —COO—, —OCO—, —O—CO—O—, —NHCO—, —CONH—, —NH—CO—O—, —O—CO—NH—, —NH—, —S—, and —CO—O—CH$_2$—CO—O—;
- $R^3$ is each independently a divalent group selected from the group consisting of: a linear, branched, or cyclic aliphatic hydrocarbon group; an aromatic hydrocarbon group; and an aliphatic heterocyclic group or aromatic heterocyclic group containing, in the skeleton, at least one group selected from the group consisting of —O—, —CO—, —COO—, —OCO—, —O—CO—O—, —NHCO—, —CONH—, —NH—CO—O—, —O—CO—NH—, —NH—, —N=, —S—, —SO—, and —SO$_2$—; and
- n is an integer of 0 or 1 to 10, with the proviso that when n is 0, $R^2$ has the hydroxyl group, and when n is from 1 to 10, at least one of $R^2$ and $R^3$ has the hydroxyl group.

9. The photoacid generator of claim 8, together with a compound that reacts with an acid.

10. The photoacid generator of claim 4, together with a compound that reacts with an acid.

* * * * *